United States Patent [19]

Smirmaul

[11] Patent Number: 4,869,716
[45] Date of Patent: Sep. 26, 1989

[54] SURGICAL INSTRUMENT AND METHOD FOR CUTTING THE LENS OF AN EYE

[76] Inventor: Heinz J. Smirmaul, 1307 Brookstone La., Duncanville, Tex. 75137

[21] Appl. No.: 261,572

[22] Filed: Oct. 24, 1988

[51] Int. Cl.$^4$ .............................................. A61B 17/20
[52] U.S. Cl. ...................................... 604/22; 128/305; 128/320
[58] Field of Search .................. 604/22; 128/305, 306, 128/307, 309, 320

[56] References Cited

U.S. PATENT DOCUMENTS

| | | | |
|---|---|---|---|
| 1,833,687 | 11/1931 | Neivert . | |
| 2,843,128 | 7/1958 | Storz | 128/309 |
| 3,739,784 | 6/1973 | Itoh | 128/320 |
| 3,835,859 | 9/1974 | Roberts et al. | 128/305 |
| 4,436,091 | 3/1984 | Banko | 128/305 |
| 4,538,611 | 9/1985 | Kelman | 604/22 |
| 4,643,187 | 2/1987 | Okada | 128/303 |
| 4,706,669 | 11/1987 | Schlegel | 604/22 |
| 4,732,150 | 3/1988 | Keener, Jr. | 128/320 |
| 4,766,897 | 8/1988 | Smirmaul | 128/305 |

Primary Examiner—Jerome L. Kruter
Attorney, Agent, or Firm—Ross, Howison, Clapp & Korn

[57] ABSTRACT

An ophthalmic surgical instrument includes a handle adapted for support in the hand of a user. A rod is attahed to the handle. An elongated tubular member is disposed adjacent to the rod and is attached to the handle. The elongated tubular member is shorter than the rod. An actuator is mounted to the handle for movement between a forward position and a rearward position with respect to the handle. A flexible elongated wire is partially disposed within the elongated tubular member. The wire is attached to the second end of the rod and is attached to the actuator, such that movement of the actuator to the forward position causes the flexible elongated wire not disposed within the elongated tubular member to bow outwardly to partially encircle the lens of the eye thereby positioning the lens between the flexible elongated wire and the rod. Movement of the actuator to the rearward position causes the flexible elongated wire to retract within the elongated tubular member and move generally parallel to the rod to cut the lens.

20 Claims, 2 Drawing Sheets

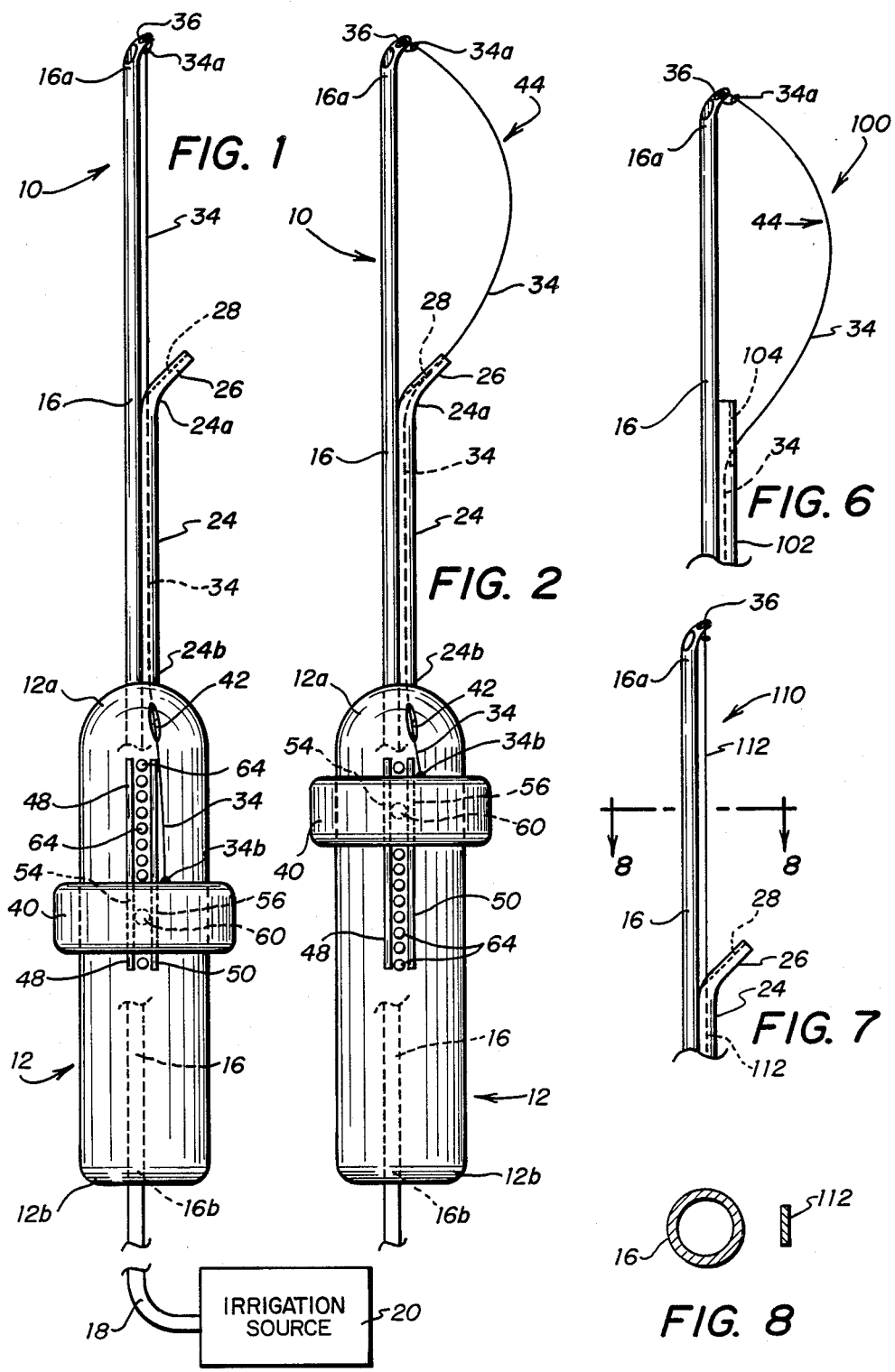

SURGICAL INSTRUMENT AND METHOD FOR CUTTING THE LENS OF AN EYE

TECHNICAL FIELD

This invention relates to surgical instruments, and more particularly to an ophthalmic surgical instrument for cutting the lens of an eye within the posterior chamber of the eye.

BACKGROUND OF THE INVENTION

The natural lens of an eye is a lenticular-shaped body having three portions. The core portion is the nucleus which is surrounded by a cortex. Enclosing the cortex and constituting the wall of the lens is the capsule. The degenerating or degenerated lens of an eye, or a localized point of degeneration within a lens is referred to as a cataract. As a result of a cataractous degeneration, the lens becomes opaque resulting in visual disability.

Numerous surgical procedures have been developed for removal of cataracted lenses including intracapsular extraction and extracapsular extraction. When the cataract is removed without breaking the capsule, such that the lens is entirely removed, an intracapsular extraction is performed. By contrast, when the forward facing, anterior portion of the capsule is removed followed by separate removal of the lens contents, an extracapsular extraction is performed. Generally, in an extracapsular extraction, the posterior portion of the lens capsule remains in the eye.

In extracapsular cataract extraction, an incision is made into the eye, and the anterior capsule is removed. The size of the nucleus dictates the size of the incision which must be made for the cataract to be extracted. Since the nucleus may be large in diameter for example, approximately 10 millimeters, an incision of 10.5 millimeters to 12 millimeters is employed with this technique. However, a smaller incision would present advantages with respect to reducing operative time, increasing post-operative wound strength, quickening healing and reducing the frequency of bleeding and infection complications. Therefore, techniques have been developed to minimize the diameter of the incision made into the eye for cataract removal. One such technique and instrument developed is described and claimed in U.S. Pat. No. 4,538,611, issued to Charles Kelman on Sept. 3, 1985 and entitled "Surgical Instrument and Method of Cutting a Lens of An Eye". An additional process is described in U.S. Pat. No. 4,732,150, issued to Gerald Keener, Jr. on Mar. 22, 1988 and entitled "Process for Cataract Extraction". In both these methods, a small incision is made into the eye and an instrument is inserted therethrough for cutting the lens into multiple sections so that smaller sections of the lens can be removed through the incision rather than the entire lens. The lens nucleus is moved into the anterior chamber of the eye and is cut into multiple sections prior to removing the individual sections through the incision. Such procedures and instruments; however, require that the lens be moved to the anterior chamber of the eye. The lens and the multiple sections cut from the lens may contact the corneal endothelium of the eye resulting in damage to this tissue.

A need has thus arisen for an ophthalmic surgical instrument and method for removing a lens of an eye while in the posterior chamber of the eye to thereby minimize any damage to the endothelium layer of the eye. In such a procedure, containment of the lens and cut portions of the lens must be accomplished within the posterior chamber prior to removal through the incision made in the eye.

SUMMARY OF THE INVENTION

In accordance with the present invention, an ophthalmic surgical instrument is provided for cutting the lens of an eye. The surgical instrument includes a handle adapted for support in the hand of a user. A rod is attached to the handle. An elongated tubular member is disposed adjacent to the rod and is attached to the handle. The elongated tubular member is shorter than the rod. An actuator is mounted to the handle for movement between a forward position and a rearward position with respect to the handle. A flexible elongated wire is partially disposed within the elongated tubular member. The wire is attached to the second end of the rod and is attached to the actuator, such that movement of the actuator to the forward position causes the flexible elongated wire not disposed within the elongated tubular member to bow outwardly to partially encircle the lens of the eye thereby positioning the lens between the flexible elongated wire and the rod. Movement of the actuator to the rearward position causes the flexible elongated wire to retract within the elongated tubular member and move generally parallel to the rod to cut the lens.

In accordance with another aspect of the present invention, a method for cutting a lens of an eye is provided. The method includes inserting into the anterior chamber of the eye a surgical instrument having a handle which is supported by the user. The surgical instrument includes a rod attached to the handle; a tubular member disposed adjacent to the rod with the first end thereof attached to the handle and the second end thereof terminating in an arcuate portion; an actuator mounted to the handle; and a flexible wire partially disposed within the tubular member. The flexible wire is attached to the rod and to the actuator. The method further includes moving the actuator to a rear position with respect to the handle, such that the flexible wire is disposed adjacent to the rod during insertion of the rod into the anterior chamber of the eye. The actuator is then moved to the forward position after the rod and tubular member have been inserted into the anterior chamber of the eye to thereby cause the flexible wire to bow outwardly from the rod in a plane parallel to the plane of the lens in the posterior chamber of the eye. The flexible wire is positioned within the posterior chamber of the eye around a portion of the lens by rotating the handle of the surgical instrument, such that the wire lies in a plane perpendicular to the plane of the lens and the lens lies between the flexible wire and the rod. The actuator is then moved rearwardly to retract the flexible wire into the tubular member, thereby cutting the lens of the eye with the flexible wire within the posterior chamber of the eye.

BRIEF DESCRIPTION OF DRAWINGS

For a more complete understanding of the present invention and for further advantages thereof, reference is now made to the following Description of the Preferred Embodiments taken in conjunction with the accompanying Drawings in which:

FIG. 1 is a top-plan view of the present surgical instrument with the actuator in the retracted position;

FIG. 2 is a top-plan view of the present surgical instrument with the actuator in the extended position;

FIG. 6 is a top-plan view of an additional embodiment of the present surgical instrument;

FIG. 7 is a top-plan view of an additional embodiment of the present surgical instrument; and FIG. 8 is a cross-sectional view of the present surgical instrument taken generally along sectional lines 8—8 of FIG. 7.

DESCRIPTION OF THE PREFERRED EMBODIMENT

Figure 3:
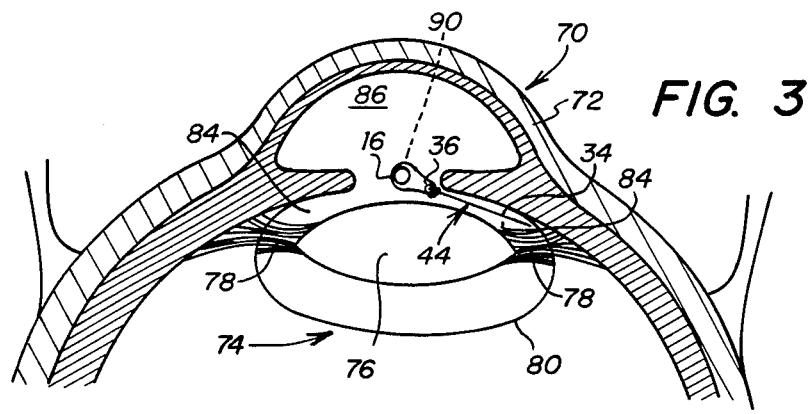
FIG. 3 is a cross-sectional view of an eye illustrating the present surgical instrument inserted in the posterior chamber with the wire extended.

Referring simultaneously to FIGS. 1 and 2, the present surgical instrument is illustrated and is generally identified by the numeral 10. Surgical instrument 10 includes a handle, generally identified by the numeral 12, having ends 12a and 12b. Handle 12 is adapted to be supported in the hand of the surgeon for use in the surgical procedure of removing a lens of the eye in accordance with the present invention. Surgical instrument 10 may have an overall length of, for example, 10–15 centimeters.

Interconnected to handle 12 is an elongated tubular member, generally identified by the numeral 16. Elongated tubular member 16 includes ends 16a and 16b, and may comprise, for example, a hollow hypodermic needle 18–21 gage. Elongated tubular member 16 extends through end 12b of handle 12, such that end 16b of elongated tubular member 16 can be interconnected to a flexible tube 18 which is interconnected to an irrigation source 20. Irrigation source 20 may comprise any standard device for providing an irrigation fluid to a surgical site, such devices being well-known to those skilled in the art. The irrigation fluid may include water or hyaluronic acid commercially available under the trademark HEALON. It therefore can be seen that elongated tubular member 16 comprises a conduit for the delivery of irrigating fluid to the surgical site.

Also attached to handle 12 is an elongated tubular member 24 which is shorter in length than elongated tubular member 16, and may comprise, for example, a hollow hypodermic needle, 18–21 gage. Elongated tubular member 24 includes ends 24a and 24b. End 24b is attached handle 12 and end 24a terminates in a arcuate portion 26. Arcuate portion 26 forms an approximate radius of 45° with respect to elongated tubular member 24 and has a length of, for example, 3–5 millimeters. Arcuate portion 26 further includes a slotted aperture 28 disposed adjacent to elongated tubular member 16.

Partially disposed within elongated tubular member 24 is a wire 34 having ends 34a and 34b. End 34a of wire 34 is attached to elongated tubular member 16 at end 16a through an aperture 36 located on end 16a of elongated tubular member 16. End 34a of wire 34 forms a loop around end 16a of elongated tubular member 16 and is secured through aperture 36 by cementing or soldering wire 34 to itself. End 34b of wire 34 is attached to an actuator 40 and passes through an aperture 42 in handle 12. Wire 34, may comprise, for example, stainless steel wire having a diameter of 0.008–0.015 inches.

Actuator 40 is positioned around handle 12 for translational motion between the position shown in FIG. 1, the retracted position, and the position shown in FIG. 2, the extended position of actuator 40. In the retracted position of actuator 40, wire 34 lies parallel to elongated tubular member 16. Slotted aperture 28 within arcuate portion 26 of elongated tubular member 24 allows wire 34 to exit elongated tubular member 24 and assume this parallel position. In the extended position of actuator 40, wire 34 bows outwardly to form a loop 44 as illustrated in FIG. 2. Loop 44 is partially caused by the arcuate portion 26 of elongated tubular member 24 which also provides stiffness to wire 34, such that loop 44 can be rotated in accordance with the present method.

Actuator 40 is movable between the retracted or rearwardmost position with respect to handle 12 illustrated in FIG. 1 to the extended or forwardmost position with respect to handle 12 as illustrated in FIG. 2. Actuator 40 is constrained to move between the two positions illustrated in FIG. 1 and FIG. 2, and is prevented from rotating with respect to handle 12 through the use of guide rails 48 and 50 disposed on handle 12. Actuator 40 includes slotted recesses 54 and 56 which mate with guide rails 48 and 50 respectively, in order to prevent rotation of actuator 40 with respect to handle 12. In order to positively position actuator 40 with respect to handle 12 and to control the size of loop 44, actuator 40 includes a detent in the form of a ball 60 disposed and held between slotted recesses 54 and 56. Ball 60 mates with a plurality of recesses 64 disposed on handle 12 between guide rails 48 and 50. Movement of actuator 40 with respect to handle 12 causes ball 60 to move between recesses 64 to thereby lock actuator 40 to handle 12 in a plurality of different positions between the positions shown in FIG. 1 and FIG. 2, the fully retracted position and fully extended position of actuator 40, respectively.

Figure 4:
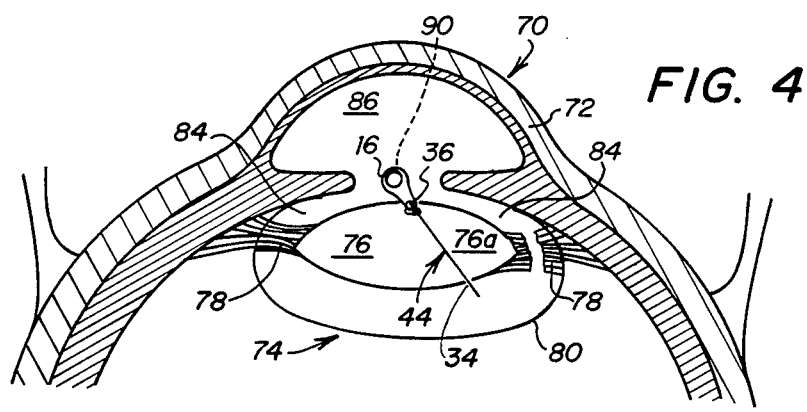
FIG. 4 is a cross-sectional view of an eye illustrating the present surgical instrument with the wire rotated around the lens to a first position.
Figure 5:
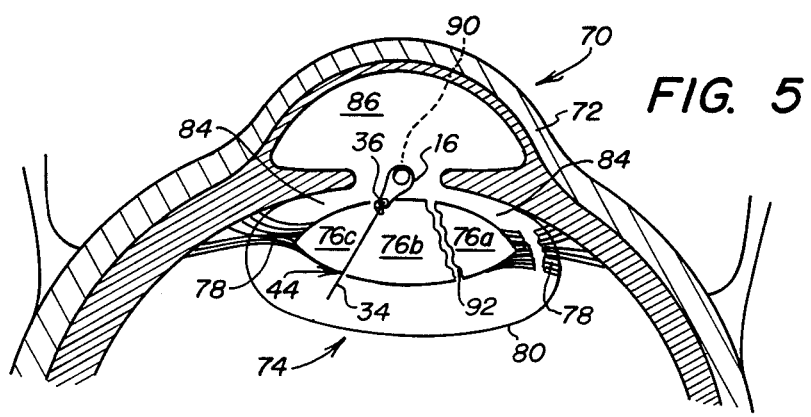
FIG. 5 is a cross-sectional view of an eye illustrating the present surgical instrument rotated to a second position having the wire extended around the lens of the eye.

Referring now simultaneously to FIGS. 3, 4 and 5, the present method of utilizing the present surgical instrument 10 for cutting the lens of an eye will be described. FIGS. 3–5 illustrate an eye generally identified by the numeral 70. Eye 70 includes cornea 72 and a lens generally identified by the numeral 74. Lens 74 includes nucleus 76, cortex 78 and capsule 80. Lens 74 is disposed within the posterior chamber 84 of eye 70 which further includes an anterior chamber 86.

An incision 90 is made through cornea 72 into anterior chamber 86 of eye 70. Surgical instruments to make incision 90 are well-known to those skilled in the art, as well as the procedure for making these incisions. The anterior capsule (not shown) of lens 7 is removed from nucleus 76. Surgical instrument 10 is then inserted through incision 90 in the retracted position of actuator 40 as shown in FIG. 1. Actuator 40 is then moved to forward position such that loop 44 is formed generally in a plane parallel to the plane of nucleus 76 within eye 70. The position of loop 44 is shown in FIG. 3. In order to cut nucleus 76, loop 44 is rotated through cortex 78 to the position shown in FIG. 4, such that wire 34 partially encircles nucleus 76. Rotation of loop 44 is accomplished from the position shown in FIG. 3 to the position shown in FIG. 4 by rotating handle 12 of surgical instrument 10. Actuator 40 is then retracted to the position of FIG. 1 such that wire 34 cuts through nucleus 76 as wire 34 is retracted. A first cut 92 (FIG. 5) of approximately one-third of nucleus 76 has therefore been made using the present surgical instrument 10.

In order to perform a second cut of nucleus 76, wire 34 is again extended by movement of actuator 40 to the extended position of FIG. 2. Loop 44 is then rotated through cortex 78 by rotation of handle 12 to the position illustrated in FIG. 5. As can be seen in FIG. 5, a portion 76a of nucleus 76 has been cut. In the position illustrated in FIG. 5 of loop 44, approximately an additional one-third of nucleus 76 is cut. Loop 44 is then retracted by operation of actuator 40 such that a second cut is made in nucleus 76 resulting in cut portions 76b and 76c of nucleus 76. During the surgical procedure of the present invention, it can be seen that elongated tubular member 16 forms a partial barrier between anterior chamber 86 and posterior chamber 84 in order to prevent cut portions of nucleus 76 from entering into anterior chamber 86 and damaging the endothelium layer of cornea 72. Although FIGS. 3, 4 and 5 illustrate the sectioning of nucleus 76 into three portions, nucleus 76 may be cut into halves or additional sections may be cut depending upon the size of nucleus 76 and the size of incision 90 performed by the surgeon. Once sectioned, the pieces of nucleus 76 are removed through incision 90 using surgical instruments well-known to those skilled in the art and the cortex material remaining in the capsule 80 is aspirated and irrigated from the eye 70 in conventional manner. Irrigating fluid to perform this portion of the surgical operation is provided through elongated tubular member 16 from irrigation source 20.

Referring now to FIG. 6, an additional embodiment of the present surgical instrument is illustrated and is generally identified by the numeral 100. Like numerals are used for like and corresponding components of surgical instrument 100 as are used to identify surgical instrument 10. Surgical instrument 100 includes an elongated tubular member 102 which lies parallel to elongated tubular member 16 throughout its entire length. Elongated tubular member 102 includes a slotted aperture 104 disposed opposite to elongated tubular member 16. Slotted aperture 104 allows wire 34 to bow outwardly in extended position as illustrated in FIG. 2 with respect to surgical instrument 10. The operation of surgical instrument 100 is similar to the operation of surgical instrument 10 previously described with respect to FIGS. 1–5.

Referring now to FIGS. 7 and 8, a further embodiment of the present surgical instrument is illustrated, and is generally identified by the numeral 110. Reference numerals for components previously identified with respect to surgical instrument 10 are used to identify corresponding elements for surgical instrument 110. Surgical instrument 110 includes a band 112 in place of wire 34. Band 112 cuts nucleus 76 of eye 70 in a manner similar to wire 34; however, due to the increased width of band 112, cut portions of nucleus 76 can be retained between band 112 and elongated tubular member 16 in order to guide the cut portions through incision 90. Surgical instrument 110 therefore functions as a surgical instrument for removing cut portions of nucleus 76 from eye 70.

It therefore can be seen that the present surgical instruments provide for the cutting of the nucleus of a lens within the posterior capsule of an eye while retaining the cut segments of the lens within the posterior chamber during the surgical procedure of removing the nucleus from the eye.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. An ophthalmic surgical instrument for cutting the lens of an eye comprising:
   a handle adapted for support in a hand of a user;
   a rod having first and second ends, said first end thereof being attached to said handle;
   an elongated tubular member disposed adjacent to said rod and having first and second ends, said first end thereof being attached to said handle, said elongated tubular member being shorter than said rod;
   actuator means mounted to said handle for movement between a forward position and a rearward position with respect to said handle;
   a flexible elongated wire having first and second ends and partially disposed within said elongated tubular member, said first end thereof being attached to said second end of said rod and said second end thereof being attached to said actuator means such that movement of said actuator means to said forward position causes said flexible elongated wire not disposed within said elongated tubular member to bow outwardly to partially encircle the lens of the eye thereby positioning the lens between said flexible elongated wire and said rod, and movement of said actuator means to said rearward position causes said flexible elongated wire to retract within said elongated tubular member and move generally parallel to said rod to cut the lens.

2. The surgical instrument of claim 1 wherein said elongated tubular member second end includes an arcuate portion.

3. The surgical instrument of claim 2 wherein said arcuate portion of said elongated tubular member includes a slotted aperture disposed adjacent said rod.

4. The surgical instrument of claim 1 wherein said actuator means includes a sleeve slidably disposed on said handle for movement between said forward position and said rearward position.

5. The surgical instrument of claim 4 wherein said handle includes a guide and said sleeve includes a slotted aperture for receiving said guide for preventing rotation of said sleeve around said handle.

6. The surgical instrument of claim 4 wherein said handle includes a plurality of recesses and said sleeve includes a detent received by said plurality of recesses for selectively positioning said sleeve with respect to said handle.

7. The surgical instrument of claim 1 and further including:
   an irrigation source connected to said rod for dispensing irrigating fluid from said irrigation source to the eye.

8. An ophthalmic surgical instrument for cutting a lens of an eye comprising:
   a handle adapted for support in a hand of a user;
   a first elongated tubular member having first and second ends, said first end thereof being attached to said handle and adapted for receiving irrigating fluid for transport to the eye;
   a second member disposed adjacent to said first elongated tubular member and having first and second ends, said first end thereof being attached to said handle and said second end terminating in an arcuate portion, said second elongated tubular member being shorter than said first elongated tubular member;

actuator means mounted to said handle for movement between a forward position and a rearward position with respect to said handle;

a flexible elongated wire having first and second ends and partially disposed within said second elongated tubular member, said first end thereof being attached to said second end of said first elongated tubular member and said second end thereof being attached to said actuator means, such that movement of said actuator means to said forward position causes said flexible elongated wire not disposed within said second elongated tubular member to bow outwardly to partially encircle the lens of the eye thereby positioning the lens between said flexible elongated wire and said first elongated tubular member, and movement of said actuator means to said rearward position causes said flexible elongated wire to retract within said second elongated tubular member and move generally parallel to said first elongated tubular member to cut the lens.

9. The surgical instrument of claim 8 wherein said arcuate portion of said second elongated tubular member includes a slotted aperture disposed adjacent to said first elongated tubular member.

10. The surgical instrument of claim 8 wherein said actuator means includes a sleeve slidably disposed on said handle for movement between said forward position and said rearward position.

11. The surgical instrument of claim 8 wherein said first end of said first elongated tubular member includes an aperture for receiving said flexible elongated wire.

12. The surgical instrument of claim 8 wherein said arcuate portion of said second elongated tubular member forms an angle of approximately 45° with said second elongated tubular member.

13. The surgical instrument of claim 12 wherein said arcuate portion of said second elongated tubular member includes a slotted aperture disposed adjacent to said first elongated tubular member.

14. The surgical instrument of claim 13 wherein said actuator means includes a sleeve slidably disposed on said handle for movement between said forward position and said rearward position.

15. The surgical instrument of claim 14 wherein said handle includes a guide and said sleeve includes a slotted aperture for receiving said guide for preventing rotation of said sleeve around said handle; and wherein said handle includes a plurality of recesses and said sleeve further includes a detent received by said plurality of recesses for selectively positioning said sleeve with respect to said handle.

16. The surgical instrument of claim 8 wherein said flexible elongated wire comprises a band of wire having a width dimension.

17. A method for cutting a lens of an eye having an anterior chamber and a posterior chamber, divided by the iris of the eye, the lens being normally disposed in the posterior chamber, comprising the steps of:

inserting into the anterior chamber of the eye a surgical instrument having a handle supported by the user, a rod having first and second ends, the first end of the rod being attached to the handle, a tubular member disposed adjacent to the rod and having first and second ends, the first end thereof being attached to the handle and the second end terminating in an arcuate portion, the tubular member being shorter than the rod, an actuator mounted to the handle, and a flexible wire having first and second ends, the flexible wire being partially disposed within the tubular member, the first end of the flexible wire being attached to the second end of the rod and the second end of the flexible wire being attached to the actuator;

moving the actuator to a rearward position with respect to the handle, such that the flexible wire is disposed adjacent to the rod during insertion of the instrument into the anterior chamber of the eye;

moving the actuator to a forward position, after the rod and tubular member have been inserted into the anterior chamber of the eye to cause the flexible wire to bow outwardly from the rod in a plane parallel to the plane of the lens of the eye in the posterior chamber of the eye;

maintaining the lens in the posterior of the eye by positioning the rod to block movement of the lens from the posterior chamber into the anterior chamber;

positioning in the posterior chamber of the eye the bowed flexible wire around a portion of the lens of the eye by rotating the handle of the surgical instrument such that the bowed flexible wire lies in a plane perpendicular to the plane to the lens and the lens lies between the flexible wire and the rod within the posterior chamber of the eye; and moving the actuator to the rearward position with respect to the handle of the surgical instrument to retract the flexible wire into the tubular member while the lens lies between the flexible wire and the rod within the posterior of the eye, thereby cutting the lens of the eye with the flexible wire within the posterior chamber of the eye.

18. The method of claim 17 in which the step of positioning in the posterior chamber the bowed flexible wire around a portion of the lens of the eye comprises the step of:

rotating the handle of the surgical instrument such that the flexible wire is positioned around approximately one-third of the lens to allow the flexible wire to form a first cut to sever approximately one-third of the lens in the posterior chamber of the eye.

19. The method of claim 18 in which the step of positioning in the posterior chamber the bowed flexible wire around a portion of the lens of the eye comprises the step of:

further rotating the handle of the surgical instrument to form a second cut of the lens to sever an additional approximately one-third of the lens.

20. The method of claim 17 and further including:

irrigating the eye by passing irrigation fluid through the rod.

* * * * *

UNITED STATES PATENT AND TRADEMARK OFFICE
CERTIFICATE OF CORRECTION

PATENT NO. : 4,869,716

DATED : SEPTEMBER 26, 1989

INVENTOR(S) : HEINZ J. SMIRMAUL

It is certified that error appears in the above-identified patent and that said Letters Patent is hereby corrected as shown below:

Column 6, Line 67

After second, insert -- elongated tubular --

Signed and Sealed this

Twenty-third Day of October, 1990

Attest:

HARRY F. MANBECK, JR.

*Attesting Officer*      *Commissioner of Patents and Trademarks*